(12) United States Patent
Ma et al.

(10) Patent No.: US 9,243,011 B2
(45) Date of Patent: Jan. 26, 2016

(54) DIALKYL(2-ALKOXY-6-AMINOPHENYL)PHOSPHINE, THE PREPARATION METHOD AND USE THEREOF

(75) Inventors: Shengming Ma, Hangzhou (CN); Bo Lv, Hangzhou (CN); Chunling Fu, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 53 days.

(21) Appl. No.: 14/114,704

(22) PCT Filed: Jul. 3, 2012

(86) PCT No.: PCT/CN2012/078129
§ 371 (c)(1),
(2), (4) Date: Oct. 29, 2013

(87) PCT Pub. No.: WO2013/166770
PCT Pub. Date: Nov. 14, 2013

(65) Prior Publication Data
US 2014/0309422 A1 Oct. 16, 2014

(30) Foreign Application Priority Data

May 10, 2012 (CN) .......................... 2012 1 0146220

(51) Int. Cl.
*C07F 9/50* (2006.01)
*C07F 9/59* (2006.01)
*B01J 31/18* (2006.01)

(52) U.S. Cl.
CPC ............... *C07F 9/591* (2013.01); *B01J 31/189* (2013.01); *C07F 9/5022* (2013.01); *B01J 2231/42* (2013.01); *B01J 2531/824* (2013.01)

(58) Field of Classification Search
USPC ....................................................... 568/8, 17
See application file for complete search history.

(56) References Cited

U.S. PATENT DOCUMENTS

2004/0171833 A1 9/2004 Buchwald et al.
2012/0197030 A1 8/2012 Ma et al.

FOREIGN PATENT DOCUMENTS

| CN | 1745049 A | 3/2006 |
|---|---|---|
| CN | 101274288 A | 10/2008 |
| CN | 101693723 A | 4/2010 |

OTHER PUBLICATIONS

Lundgren; Angewandte Chemie International edition; 49, 4071-4074, published on Apr. 30, 2010.*
International Search Report Issued in PCT/CN2012/078129, mailed on Feb. 28, 2013.
PCT/ISA/237—Mailed on Feb. 28, 2013, issued in PCT/CN2012/078129.

* cited by examiner

*Primary Examiner* — Sudhakar Katakam
*Assistant Examiner* — Pancham Bakshi
(74) *Attorney, Agent, or Firm* — Birch, Stewart, Kolasch & Birch, LLP

(57) ABSTRACT

The present invention relates to the compound of dialkyl(2-alkoxy-6-aminophenyl)phosphine and the preparation method thereof and the application in the palladium catalyzed coupling reactions of aryl chloride and ketone. The dialkyl (2-alkoxy-6-aminophenyl)phosphine of the present invention could coordinate with the palladium catalyst to highly selectively activate the inert carbon-chlorine bond, and to catalyze direct arylation reaction in the α-position of ketones to produce corresponding coupling compounds. The preparation method of the present invention is a simple one-step method which produces the air-stable dialkyl(2-alkoxy-6-aminophenyl)phosphine. Compared with the synthetic routes of ligands to be used in the activation of carbon-chlorine bonds in the prior arts, the preparation method of the present invention has the advantages of short route and easy operation.

3 Claims, No Drawings

DIALKYL(2-ALKOXY-6-AMINOPHENYL)PHOSPHINE, THE PREPARATION METHOD AND USE THEREOF

FIELD OF THE INVENTION

The present invention relates to the compound of dialkyl (2-alkoxy-6-aminophenyl)phosphine, the preparation method of simple one-step synthesis, and application in the palladium catalyzed coupling reaction between aryl chloride and ketone. To be more specific, the present invention provides the preparation method of producing the air-stable dialkyl(2-alkoxy-6-aminophenyl)phosphine and its application in the reaction system of coordinating with the palladium catalyst to couple aryl chloride with ketone in the system.

BACKGROUND OF THE TECHNOLOGY

Organic halides are very important building blocks in organic synthesis. However, in the application in the past, expensive but relatively more active organic bromides and iodides were used in coupling reactions to synthesize target molecules (*Chem. Rev.* 1994, 94, 1047). So far, some examples of coupling reaction between aryl chloride and ketone have been reported (*Acc. Chem. Res.* 2003, 36, 234; *Angew. Chem. Int. Ed.* 2010, 49, 676; *Chem. Rev.* 2010, 110, 1082), but there still exist the following problems.

1. The ligand in most catalyst systems are of complicated structure and difficult to synthesize which lead to significant costs.
2. Many existing catalyst systems fail to highly selectively catalyze the mono-arylation of ketone with acetyl group.
3. There has been few studies on arylation of acetone. It is hard for many aryl chlorides with substituted electron withdrawing groups to be introduced into the α-position of the carbonyl of acetone.

The objective of the present invention is to disclose a novel organic phosphine ligand and thereby solve the above problems.

SUMMARY OF THE INVENTION

In view of said problems in the prior arts, the present invention provides a novel compound of organic phosphine ligand dialkyl(2-alkoxy-6-aminophenyl)phosphine, the preparation method thereof and the its application in coupling reactions of aryl chloride and ketone highly selectively catalyzed by said organic phosphine and palladium.

The detailed technical solutions of the present invention are as follows.

According to a first aspect of the invention there is provided a compound of dialkyl(2-alkoxy-6-aminophenyl)phosphine, represented by the below formula.

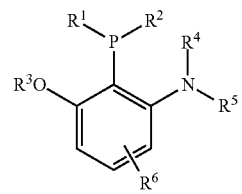

Wherein each $R^1$ and $R^2$ is independently selected from the group consisting of isopropyl, cyclopentyl, tertbutyl, cyclohexyl or admantyl group;

$R^3$ is either alkyl or aryl;

each of $R^4$ and $R^5$ is independently selected from alkyl or aryl;

$R^6$ is selected from substituted alkyl, alkoxyl, aryl, amino, thiol, carbonyl or cyano, with unfixed substituent position, occupying either the two meta positions or the para position, the number is 0-3.

According to a second aspect of the invention there is provided the preparation method of dialkyl(2-alkoxy-6-aminophenyl)phosphine of the present invention, wherein trichlorophosphine, alkylmagnesium chloride, alkoxy substituted phenyl amine and n-butyl lithium are used as starting materials. Alkoxy substituted phenyl amine is reacted with n-butyl lithium in tetrahydrofuran to produce the corresponding lithium reagent. Alkylmagnesium chloride is reacted with trichlorophosphine to produce chlorodialkyl phosphine. The above mentioned lithium reagent is reacted with chlorodialkyl phosphine to produce dialkyl(2-alkoxy-6-aminophenyl)phosphine. The pure product of dialkyl(2-alkoxy-6-aminophenyl)phosphine could be obtained after re-crystallization.

The preparation method of dialkyl(2-alkoxy-6-aminophenyl)phosphine, comprising the following steps:

1) using n-Hexane as an organic solvent, the alkoxy substituted phenyl amine is reacted with n-butyl lithium at 80° C. for 2~15 hours to produce the corresponding lithium reagent 2-$R^3$O-6-$R^4R^5$N—$(R^6)_n$C$_6$H$_{(3-n)}$Li;

2) the said lithium reagent above 2-$R^3$O-6-$R^4R^5$N—$(R^6)_n$C$_6$H$_{(3-n)}$Li is reacted with chlorodialkyl phosphine $R^1R^2$PCl at −78~80° C. for 2~10 hours to produce dialkyl(2-alkoxyl-6-aminophenyl)phosphine 2-$R^3$O-6-$R^4R^5$N—$(R^6)_n$C$_6$H$_{(3-n)}$P$R^1R^2$; wherein the molar ratio of said chlorodialkyl phosphine and 2-alkoxyl-6-aminophenyl lithium is 0.8~1.2:1;

said $R^1$, $R^2$, $R^3$, $R^4$, $R^5$ and $R^6$ are as described in claim 1.

The said dialkyl(2-alkoxy-6-aminophenyl)phosphine of the present invention is purified by recrystallization.

A typical reaction formula is as follows:

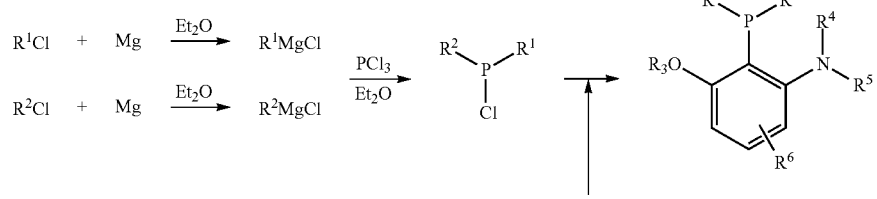

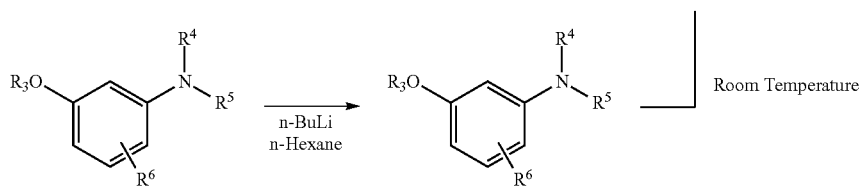

Wherein each $R^1$ and $R^2$ is independently selected from the group consisting of isopropyl, tertbutyl, cyclopentyl, cyclohexyl or admantyl group; $R^3$ is either alkyl or aryl; each of $R^4$ and $R^5$ is independently selected from alkyl or aryl; $R^6$ is selected from substituted alkyl, alkoxyl, aryl, amino, thiol, carbonyl or cyano, the number is 0-3.

According to a second aspect of the invention there is provided the application of the said dialkyl(2-alkoxy-6-aminophenyl)phosphine in the coupling reaction of aryl chloride and ketone to produce coupling compounds, wherein the synthesis of the corresponding coupling compounds are carried out under the protection of inert gases at 80~120° C. by stirring base, palladium, dialkyl(2-alkoxyl-6-aminophenyl)phosphine, ketone and aryl chloride in an organic solvent for 0.6~50 hours to produce the corresponding coupling compounds; wherein the equivalent molar ratio of said base, palladium catalyst, dialkyl(2-alkoxyl-6-aminophenyl)phosphine, ketone and aryl chloride is 1.0~4.0:0.01~0.05:0.015~0.075:1.0~4.0:1.0; said organic solvent is toluene, benzene, xylene, dioxane or acetone; said base is potassium carbonate, potassium phosphate, cesium carbonate, sodium tert-butoxide, potassium tert-butoxide or cesium fluoride; said palladium is palladium acetate, palladium chloride, tris(dibenzylideneacetone)dipalladium, palladium(π-cinnamyl) chloride or allylpalladium chloride; dialkyl(2-alkoxy-6-aminophenyl)phosphine is as described in claim 1; said aryl chloride is $R^7$ substituted chlorbenzene; said ketone is $R^8COCH_2R^9$; $R^7$ is ortho-, meta-, para-substituted alkyl, amino or alkoxy; $R^8$ is substituted aryl, alkyl or heterocyclic group; $R^9$ is hydrogen, substituted aryl, alkyl or heterocyclic group.

The typical coupling reaction of aryl chloride and ketone could be demonstrated by the following reaction formula:

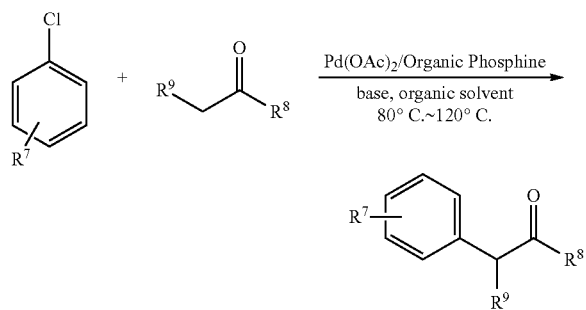

$R^7$ is ortho-, meta-, para-substituted alkyl, amino or alkoxy; $R^8$ is substituted aryl, alkyl or heterocyclic group; $R^9$ is hydrogen, substituted aryl, alkyl or heterocyclic group; said organic solvent is toluene, benzene, xylene, dioxane or acetone; said base is potassium carbonate, potassium phosphate, cesium carbonate, sodium tert-butoxide, potassium tert-butoxide or cesium fluoride; said palladium is palladium acetate, palladium chloride, tris(dibenzylideneacetone)dipalladium, palladium(π-cinnamyl) chloride or allylpalladium chloride; and said organic phosphine is dialkyl(2-alkoxy-6-aminophenyl)phosphine.

The beneficial effects of the present invention are as follows:

The dialkyl(2-alkoxy-6-aminophenyl)phosphine of the present invention coordinates with the palladium catalyst to activate the inert carbon-chlorine bond and catalyze direct arylation reactions of ketones in the α-position to produce corresponding compounds. Compared with the synthetic routes of ligands in the prior arts used in activating carbon-chlorine bonds, the preparation method of the present invention has the advantages of short route and easy operation, which indicates great significance of the research and practical value.

The present invention relates to the structure, of the novel compound dialkyl(2-alkoxy-6-aminophenyl)phosphine, the preparation method thereof, as well as its application in the palladium catalyzed coupling reactions of aryl chloride and ketone. Specifically, the air-stable dialkyl(2-alkoxy-6-aminophenyl)phosphine is synthesized and coordinates with the palladium catalyst to activate the $SP^2$ carbon-chlorine bond, then catalyzed the direct arylation reactions of ketones in the α-position in the reaction system to produce corresponding compounds.

The present invention provides a simple one-step preparation method to synthesize air-stable dialkyl(2-alkoxy-6-aminophenyl)phosphine. The present invention develops a highly efficient preparation method of the novel organic phosphine ligand compound (dialkyl(2-alkoxy-6-aminophenyl)phosphine) to activate inert carbon-chlorine bond and its application in the coupling reaction of aryl chlorides and ketones. Compared with the synthetic routes of ligands in the prior arts used in the activation of carbon-chlorine bonds, the preparation method of the present invention is of short route and easy to operate.

EMBODIMENTS OF THE INVENTION

The present invention will be further demonstrated in the following description of exemplary embodiments which are given for illustration of said invention and are not intended to be limited thereof.

Example 1

Synthesis of 2-Methoxy-6-piperidylphenyl(dicyclohexyl)phosphine

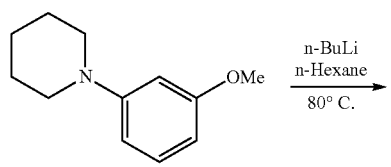

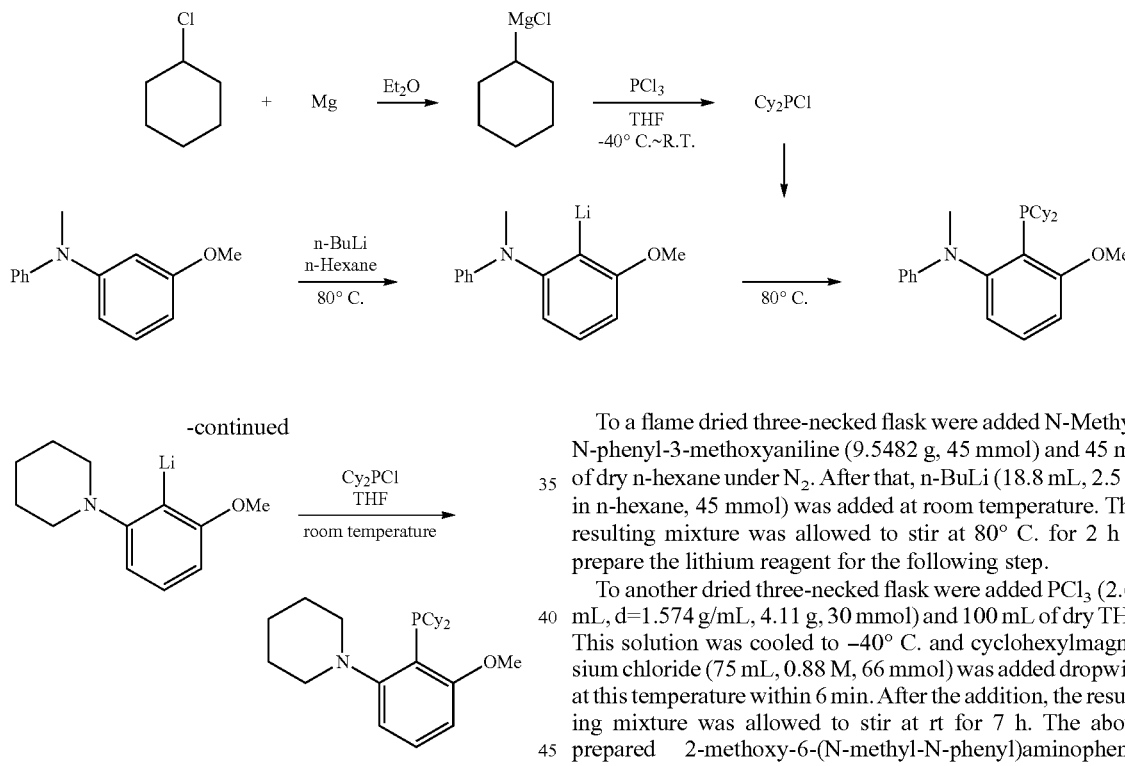

To a flame dried Schlenk vessel were added 1-(3'-Methoxyphenyl)piperidine (385.1 mg, 2.0 mmol) and 2 mL of dry n-hexane under $N_2$. After that, n-BuLi (0.83 mL, 2.5 M in n-hexane, 2 mmol) was added at room temperature. This resulting mixture was allowed to stir at 80° C. for further 3 h to prepare the lithium reagent. When the reaction vessel was cooled down to room temperature, a solution of $Cy_2PCl$ (232.7 mg, 1 mmol) in 4 mL of THF was added at room temperature to stir for 13 h. This resulting mixture was quenched with 10 mL of water, extracted with ethyl acetate (50 mL×2), washed with 20 mL of brine, and dried over anhydrous $Na_2SO_4$. Filtration, evaporation, and purified by column chromatography on silica gel afforded product (300.4 mg, yield 77%) (petroleum ether/ethyl acetate/triethyl amine=100/1/1) as a solid: m.p.: 101-102° C. (methanol); $^1$H NMR (300 MHz, $CDCl_3$) δ 7.24 (t, J=8.1 Hz, 1H, ArH), 6.71 (dd, $J_1$=7.5 Hz, $J_2$=3.6 Hz, 1H, ArH), 6.56 (d, J=8.1 Hz, 1H, ArH), 3.78 (s, 3H, $CH_3$), 2.98-2.79 (m, 4H, 2×$CH_2$), 2.40-2.20 (m, 2H, 2×CH), 1.97-1.83 (m, 2H, $CH_2$), 1.83-1.49 (m, 12H, 6×$CH_2$), 1.49-1.07 (m, 10H, 5×$CH_2$), 1.07-0.88 (m, 2H, $CH_2$); $^{13}$C NMR (75 MHz, $CDCl_3$) δ 163.3 (d, J=2.6 Hz), 162.4 (d, J=18.7 Hz), 130.2, 120.5 (d, J=27.4 Hz), 113.1 (d, J=3.2 Hz), 106.0, 55.04, 54.96, 34.8 (d, J=13.7 Hz), 32.5 (d, J=24.2 Hz), 30.5 (d, J=9.7 Hz), 27.4 (d, J=7.1 Hz), 27.1 (d, J=13.5 Hz), 26.5, 25.9, 24.3; $^{31}$P NMR (121 MHz, $CDCl_3$) δ −3.24; IR (KBr) v ($cm^{−1}$) 2932, 2911, 2845, 2806, 1578, 1568, 1455, 1423, 1380, 1253, 1231, 1217, 1113, 1084, 1027, 1003; MS (70 eV, EI) m/z (%): 388 ($M^+$+1, 5.04), 387 ($M^+$, 20.03), 222 (100); Anal. Calcd for $C_{24}H_{38}NOP$: C, 74.38; H, 9.88; N, 3.61. Found: C, 74.06; H, 9.96; N, 3.70.

Example 2

Synthesis of 2-Methoxy-6-(N-methyl-N-phenyl-amino)phenyl(dicyclohexyl)phosphine To a flame dried three-necked flask were added N-Methyl-N-phenyl-3-methoxyaniline (9.5482 g, 45 mmol) and 45 mL of dry n-hexane under $N_2$. After that, n-BuLi (18.8 mL, 2.5 M in n-hexane, 45 mmol) was added at room temperature. This resulting mixture was allowed to stir at 80° C. for 2 h to prepare the lithium reagent for the following step.

To another dried three-necked flask were added $PCl_3$ (2.61 mL, d=1.574 g/mL, 4.11 g, 30 mmol) and 100 mL of dry THF. This solution was cooled to −40° C. and cyclohexylmagnesium chloride (75 mL, 0.88 M, 66 mmol) was added dropwise at this temperature within 6 min. After the addition, the resulting mixture was allowed to stir at rt for 7 h. The above prepared 2-methoxy-6-(N-methyl-N-phenyl)aminophenyl lithium solution was then added in one portion. After 12 h with stirring at 80° C., the resulting mixture was quenched with 100 mL of water. $CH_2Cl_2$ (100 mL) and HCl aqueous solution (20 mL, 5%) were then added and the resulting mixture was extracted with $CH_2Cl_2$ (100×2 mL). The organic layers were combined, washed with 100 mL of a saturated $NaHCO_3$ aqueous solution, and dried over anhydrous $Na_2SO_4$. Filtration, evaporation and recrystallization from methanol/ethyl acetate afforded product (6.3588 g, 52% from $PCl_3$) as a white solid: m. p.: 169-170° C. (methanol/ethyl acetate); $^1$H NMR (300 MHz, $CDCl_3$) δ 7.36 (t, J=8.0 Hz, 1H, ArH), 7.20-7.09 (m, 2H, ArH), 6.84-6.73 (m, 2H, ArH), 6.68 (t, J=7.2 Hz, 1H, ArH), 6.54 (d, J=8.1 Hz, 2H, ArH), 3.87 (s, 3H, $OCH_3$), 3.22 (s, 3H, $NCH_3$), 2.42-2.26 (m, 2H, 2×CH), 1.92-1.55 (m, 8H, 4×$CH_2$), 1.42-0.86 (m, 12H, 6×$CH_2$); $^{13}$C NMR (75 MHz, $CDCl_3$) δ 163.8 (d, J=3.3 Hz), 156.7 (d, J=23.8 Hz), 149.8, 131.6, 128.4, 125.3 (d, J=26.9 Hz), 121.8 (d, J=3.9 Hz), 116.2, 113.3, 108.5, 55.3, 41.0 (d, J=7.4 Hz), 35.0 (d, J=12.0 Hz), 32.9 (d, J=25.0 Hz), 30.9 (d, J=8.1 Hz), 27.6 (d, J=8.1 Hz), 27.2 (d, J=14.2 Hz), 26.3; $^{31}$P NMR (121 MHz, $CDCl_3$) 6-3.30; IR (KBr) v ($cm^{−1}$) 2914, 2846, 1601, 1582, 1568, 1499, 1472, 1455, 1439, 1347, 1301, 1247, 1185, 1171, 1106, 1079, 1055; MS (70 eV, EI) m/z (%): 410 (M$^+$+1, 2.02), 409 (M$^+$, 9.31), 245 (100); Anal. Calcd. for C$_{26}$H$_{36}$NOP: C, 76.25; H, 8.86; N, 3.42. Found: C, 76.03; H, 8.88; N, 3.55.

Example 3

Synthesis of 2-(4'-Methoxyphenyl)-1-phenyl-1-propanone

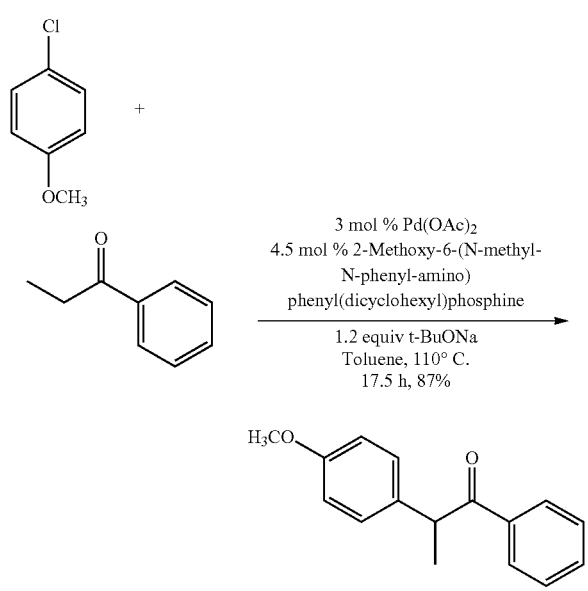

To a flame-dried and nitrogen filled Schlenk vessel were added Pd(OAc)$_2$ (6.7 mg, 0.030 mmol), 2-Methoxy-6-(N-methyl-N-phenyl-amino)phenyl(dicyclohexyl)phosphine (18.3 mg, 0.045 mmol), t-BuONa (115.4 mg, 1.2 mmol), and p-methoxyphenyl chloride (142.1 mg, 1.0 mmol)) in 1.5 mL of toluene sequentially. After being stirred for about 2 min at room temperature, propiophenone (160.9 mg, 1.2 mmol) in 1.5 mL of toluene were added. The resulting mixture was heated at 110° C. with a preheated oil bath. After 17.5 h, the reaction was complete as monitored by GC. The reaction mixture was then cooled and quenched with 10 mL of Et$_2$O. After transferring the mixture into separatory funnel, the reactor was further washed with 10 mL of Et$_2$O and 10 mL of HCl aqueous solution (5%). The combined mixture was extracted with Et$_2$O (10 mL×2), washed with 20 mL of saturated NaHCO$_3$ aqueous solution, and dried over anhydrous Na$_2$SO$_4$. Filtration, evaporation, and purification by chromatography (petroleum ether/ethyl acetate=80/1) on silica gel afforded 2-(4'-Methoxyphenyl)-1-phenyl-1-propanone (209.4 mg, 87%) as a liquid: $^1$H NMR (300 MHz, CDCl$_3$) δ 8.00-7.92 (m, 2H, ArH), 7.52-7.43 (m, 1H, ArH), 7.42-7.35 (m, 2H, ArH), 7.24-7.18 (m, 2H, ArH), 6.86-6.80 (m, 2H, ArH), 4.65 (q, J=6.9 Hz, 1H, CH), 3.75 (s, 3H, OCH$_3$), 1.52 (d, J=6.9 Hz, 3H, CH$_3$); $^{13}$C NMR (75 MHz, CDCl$_3$) δ 200.5, 158.4, 136.5, 133.4, 132.6, 128.73, 128.69, 138.4, 114.3, 55.1, 46.9, 19.5; IR (neat) ν (cm$^{-1}$) 3061, 2972, 2931, 2836, 1682, 1609, 1596, 1511, 1448, 1302, 1248, 1221, 1178, 1034, 1002; MS (70 eV, EI) m/z (%): 240 (M$^+$, 4.46), 135 (100).

Example 4

Synthesis of 2-(3'-Methoxyphenyl)-1-phenyl-1-enthanone

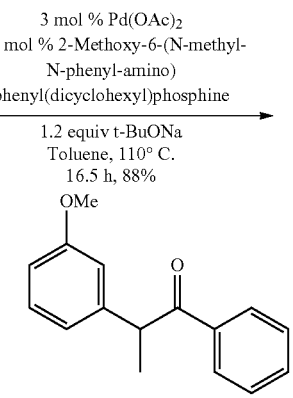

This reaction is carried out in the same manner as the reaction in example 3. The difference is that, the reactants are m-methoxyphenyl chloride (143.4 mg, 1.0 mmol), propiophenone (160.6 mg, 1.2 mmol), palladium acetate (6.6 mg, 0.029 mmol), 2-Methoxy-6-(N-methyl-N-phenyl-amino)phenyl(dicyclohexyl)phosphine (18.4 mg, 0.045 mmol), t-BuONa (115.0 mg, 1.2 mmol) in 3 mL dry toluene at 110° C. for 16.5 h. 2-(3'-Methoxyphenyl)-1-phenyl-1-enthanone (212.6 mg) was obtained with a yield of 88% as liquid. $^1$H NMR (300 MHz, CDCl$_3$) δ 8.02-7.96 (m, 2H, ArH), 7.46-7.39 (m, 1H, ArH), 7.38-7.30 (m, 2H, ArH), 7.21 (t, J=8.0 Hz, 1H, ArH), 6.94-6.88 (m, 2H, ArH), 6.77-6.72 (m, 1H, ArH), 4.69 (q, J=6.9 Hz, 1H, CH), 3.71 (s, 3H, OCH$_3$), 1.56 (d, J=6.9 Hz, 3H, CH$_3$); $^{13}$C NMR (75 MHz, CDCl$_3$) δ 199.8, 159.8, 142.8, 136.2, 132.5, 129.7, 128.5, 128.2, 119.9, 113.3, 111.8, 54.8, 47.6, 19.2; IR (neat) ν (cm$^{-1}$) 3059, 2973, 2932, 2835, 1682, 1598, 1486, 1455, 1372, 1312, 1263, 1215, 1181, 1149, 1045, 1002; MS (70 eV, EI) m/z (%): 241 (M$^+$+1, 2.10), 240 (M$^+$, 11.90), 105 (100).

Example 5

Synthesis of 1-Phenyl-2-(m-tolyl)-1-propanone

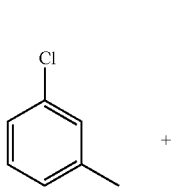

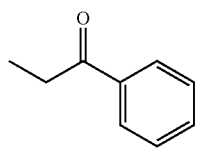

3 mol % Pd(OAc)$_2$
4.5 mol % 2-Methoxy-6-(N-methyl-N-phenyl-amino)phenyl(dicyclohexyl)phosphine 1.2 equiv t-BuONa
Toluene, 110° C.
16.5 h, 85%

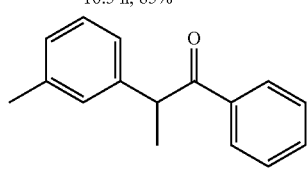

This reaction is carried out in the same manner as the reaction in example 3. The difference is that, the reactants are p-methyphenyl chloride (126.6 mg, 1.0 mmol), propiophenone (161.1 mg, 1.2 mmol), palladium acetate (6.6 mg, 0.029 mmol), 2-Methoxy-6-(N-methyl-N-phenyl-amino)phenyl(dicyclohexyl)phosphine (18.4 mg, 0.045 mmol), t-BuONa (115.4 mg, 1.2 mmol) in 3 mL dry toluene at 110° C. for 16.5 h. 1-Phenyl-2-(m-tolyl)-1-propanone (190.0 mg) was obtained with a yield of 85% as liquid. $^1$H NMR (300 MHz, CDCl$_3$) δ 8.10-7.94 (m, 2H, ArH), 7.52-7.44 (m, 1H, ArH), 7.44-7.35 (m, 2H, ArH), 7.25-7.18 (m, 1H, ArH), 7.17-7.10 (m, 2H, ArH), 7.07-7.02 (m, 1H, ArH), 4.69 (q, J=6.8 Hz, 1H, CH), 2.33 (s, 3H, ArCH$_3$), 1.57 (d, J=6.8 Hz, 3H, CH$_3$); $^{13}$C NMR (75 MHz, CDCl$_3$) δ 200.2, 141.3, 138.5, 136.4, 132.6, 128.73, 128.66, 128.3, 128.2, 127.6, 124.8, 47.7, 21.3, 19.4; IR (neat) v (cm$^{-1}$) 3058, 3025, 2975, 2930, 2870, 1682, 1605, 1596, 1583, 1488, 1448, 1372, 1338, 1238, 1208, 1181, 1158, 1075, 1002; MS (70 eV, EI) m/z (%): 224 (M$^+$, 4.20), 105 (100).

Example 6

Synthesis of 1,2-Di(4'-methoxyphenyl)-1-propanone

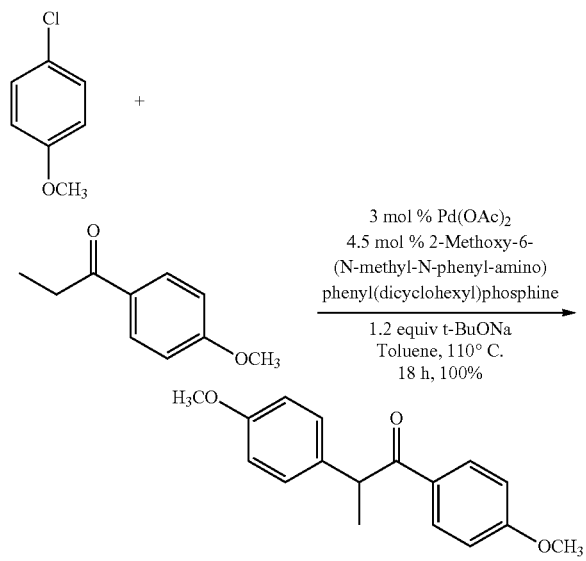

This reaction is carried out in the same manner as the reaction in example 3. The difference is that, the reactants are p-methoxyphenyl chloride (142.7 mg, 1.0 mmol), 1-(4-methoxyphenyl)-1-propanone (195.8 mg, 1.2 mmol), palladium acetate (6.6 mg, 0.029 mmol), 2-Methoxy-6-(N-methyl-N-phenyl-amino)phenyl(dicyclohexyl)phosphine (18.2 mg, 0.045 mmol), t-BuONa (115.9 mg, 1.2 mmol) in 3 mL dry toluene at 110° C. for 18 h. 1,2-Di(4'-methoxyphenyl)-1-propanone (272.1 mg) was obtained with a yield of 100% as liquid. $^1$H NMR (300 MHz, CDCl$_3$) δ 7.99-7.92 (m, 2H, ArH), 7.24-7.18 (m, 2H, ArH), 6.87-6.79 (m, 4H, ArH), 4.61 (q, J=6.9 Hz, 1H, CH), 3.76 (s, 3H, OCH$_3$), 3.71 (s, 3H, OCH$_3$), 1.50 (d, J=6.9 Hz, 3H, CH$_3$); $^{13}$C NMR (75 MHz, CDCl$_3$) δ 198.9, 163.0, 158.2, 133.8, 130.8, 129.2, 128.5, 114.1, 113.5, 55.1, 54.9, 46.3, 19.4; IR (neat) v (cm$^{-1}$) 2969, 2932, 2837, 1668, 1600, 1574, 1514, 1455, 1419, 1371, 1303, 1258, 1169, 1114, 1032; MS (70 eV, EI) m/z (%): 270 (M$^+$, 4.28), 135 (100).

Example 7

Synthesis of 2-Phenyl-1-(p-tolyl)-1-propanone

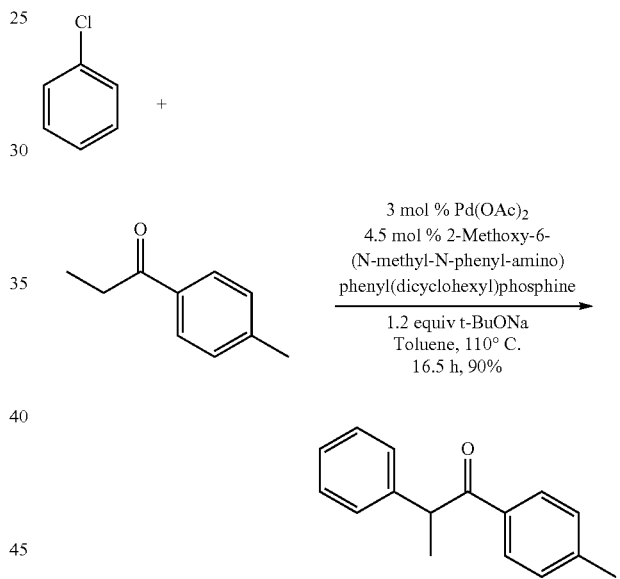

This reaction is carried out in the same manner as the reaction in example 3. The difference is that, the reactants are phenyl chloride (111.0 mg, 0.99 mmol), 1-(4-methylphenyl)-1-propanone (177.8 mg, 1.2 mmol), palladium acetate (6.7 mg, 0.030 mmol), 2-Methoxy-6-(N-methyl-N-phenyl-amino)phenyl(dicyclohexyl)phosphine (18.4 mg, 0.045 mmol), t-BuONa (115.8 mg, 1.2 mmol) in 3 mL dry toluene at 110° C. for 16.5 h. 2-Phenyl-1-(p-tolyl)-1-propanone (216.5 mg, contaminated with 11.9% of 1-(4-methylphenyl)propanone determined by $^1$H NMR) was obtained with a yield of 90% as liquid. $^1$H NMR (300 MHz, CDCl$_3$) δ 7.87-7.80 (m, 2H, ArH), 7.30-7.20 (m, 4H, ArH), 7.20-7.08 (m, 3H, ArH), 4.64 (q, J=7.0 Hz, 1H, CH), 2.27 (s, 3H, ArCH$_3$), 1.50 (d, J=7.0 Hz, 3H, CH$_3$); $^{13}$C NMR (75 MHz, CDCl$_3$) δ 199.7, 143.3, 141.6, 133.7, 129.0, 128.74, 128.72, 127.5, 126.6, 47.5, 21.3, 19.3; IR (neat) v (cm$^{-1}$) 3061, 3028, 2975, 2930, 2870, 1682, 1606, 1570, 1492, 1452, 1408, 1372, 1332, 1304, 1253, 1225, 1210, 1177, 1008; MS (70 eV, EI) m/z (%): 224 (M+, 0.64), 119 (100).

Example 8

Synthesis of 2-(2'-Methoxyphenyl)-1-phenyl-1-propanone

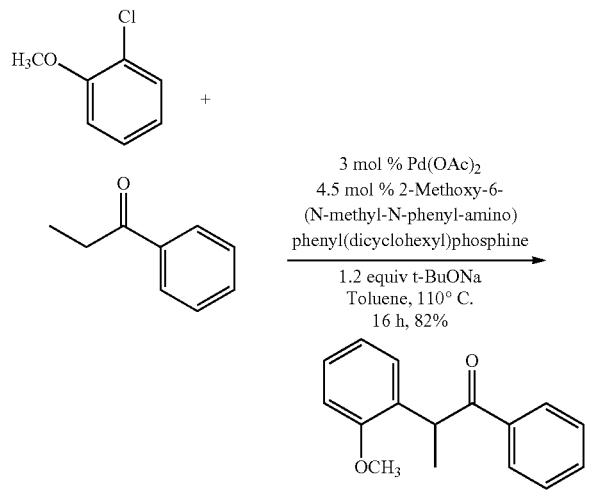

This reaction is carried out in the same manner as the reaction in example 3. The difference is that, the reactants are o-methoxyphenyl chloride (144.1 mg, 1.0 mmol), propiophenon (161.3 mg, 1.2 mmol), palladium acetate (6.7 mg, 0.030 mmol), 2-Methoxy-6-(N-methyl-N-phenyl-amino)phenyl(dicyclohexyl)phosphine (18.4 mg, 0.045 mmol), t-BuONa (115.5 mg, 1.2 mmol) in 3 mL dry toluene at 110° C. for 16 h. 2-(2'-Methoxyphenyl)-1-phenyl-1-propanone (198.8 mg) was obtained with a yield of 80% as liquid. $^1$H NMR (300 MHz, CDCl$_3$) δ 8.04-7.98 (m, 2H, ArH), 7.50-7.42 (m, 1H, ArH), 7.41-7.33 (m, 2H, ArH), 7.24-7.13 (m, 2H, ArH), 6.92-6.86 (m, 2H, ArH), 5.13 (q, J=6.9 Hz, 1H, CH), 3.87 (s, 3H, OCH$_3$), 1.51 (d, J=6.9 Hz, 3H, CH$_3$); $^{13}$C NMR (75 MHz, CDCl$_3$) δ 201.2, 155.6, 136.4, 132.4, 130.0, 128.4, 128.2, 127.9, 120.9, 110.7, 55.3, 40.2, 17.5; IR (neat) v (cm$^{-1}$) 3063, 2974, 2933, 2871, 2837, 1682, 1597, 1584, 1493, 1449, 1371, 1326, 1291, 1245, 1222, 1182, 1113, 1061, 1050, 1028, 1002; MS (70 eV, EI) m/z (%): 241 (M++1, 1.81), 240 (M+, 9.60), 135 (100).

Example 9

1-(4'-Fluorophenyl)-2-(4'-methoxyphenyl)-1-propanone

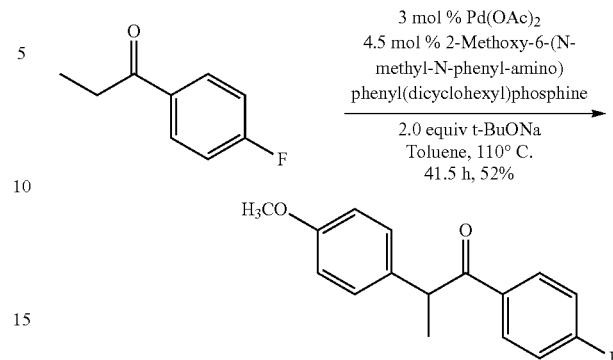

This reaction is carried out in the same manner as the reaction in example 3. The difference is that, the reactants are p-methoxyphenyl chloride (142.8 mg, 1.0 mmol), 1-(4-fluorophenyl)-1-propanone (183.5 mg, 1.2 mmol), palladium acetate (6.7 mg, 0.030 mmol), 2-Methoxy-6-(N-methyl-N-phenyl-amino)phenyl(dicyclohexyl)phosphine (18.3 mg, 0.045 mmol), t-BuONa (115.6 mg, 1.2 mmol) in 3 mL dry toluene at 110° C. for 18.5 h. 1-(4'-Fluorophenyl)-2-(4'-methoxyphenyl)-1-propanone (206.7 mg) was obtained with a yield of 80% as liquid. $^1$H NMR (300 MHz, CDCl$_3$) δ 8.01-7.93 (m, 2H, ArH), 7.22-7.15 (m, 2H, ArH), 7.14-6.99 (m, 2H, ArH), 6.87-6.80 (m, 2H, ArH), 4.59 (q, J=7.0 Hz, 1H, CH), 3.74 (s, 3H, OCH$_3$), 1.50 (d, J=7.0 Hz, 3H, CH$_3$); $^{13}$C NMR (75 MHz, CDCl$_3$) δ 198.8, 165.3 (d, J=252.7 Hz), 158.5, 133.3, 132.8 (d, J=2.6 Hz), 131.3 (d, J=8.6 Hz), 128.6, 115.4 (d, J=21.2 Hz), 114.4, 55.1, 47.0, 19.4; $^{19}$F NMR (282 MHz, CDCl$_3$) δ −105.7; IR (neat) v (cm$^{-1}$) 3071, 2974, 2932, 2869, 2837, 1682, 1598, 1514, 1505, 1455, 1409, 1372, 1336, 1302, 1247, 1180, 1157, 1114, 1101, 1035, 1006; MS (70 eV, EI) m/z (%): 259 (M++1, 1.10), 258 (M+, 6.27), 135 (100); HRMS calcd for C$_{16}$H$_{15}$O$_2$F (M+): 258.1056. Found: 258.1057.

Example 10

1-(2'-Fluorophenyl)-2-(4'-methoxyphenyl)-1-propanon

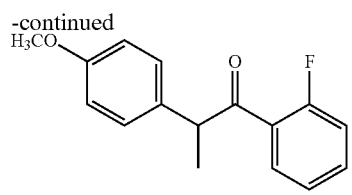

This reaction is carried out in the same manner as the reaction in example 3. The difference is that, the reactants are p-methoxyphenyl chloride (142.3 mg, 1.0 mmol), 1-(2-fluorophenyl)-1-propanone (304.2 mg, 2.0 mmol), palladium acetate (6.8 mg, 0.030 mmol), 2-Methoxy-6-(N-methyl-N-phenyl-amino)phenyl(dicyclohexyl)phosphine (18.4 mg, 0.045 mmol), t-BuONa (192.7 mg, 2.0 mmol) in 3 mL dry toluene at 110° C. for 41.5 h. 1-(2'-Fluorophenyl)-2-(4'-methoxyphenyl)-1-propanon (134.7 mg) was obtained with a yield of 52% as liquid. $^1$H NMR (300 MHz, CDCl$_3$) δ 7.76-7.68 (m, 1H, ArH), 7.44-7.34 (m, 1H, ArH), 7.20-7.08 (m, 3H, ArH), 7.07-6.98 (m, 1H, ArH), 6.83-6.77 (m, 2H, ArH), 4.57 (q, J=6.9 Hz, 1H, CH), 3.73 (s, 3H, OCH$_3$), 1.52 (d, J=6.9 Hz, 3H, CH$_3$); $^{13}$C NMR (75 MHz, CDCl$_3$) δ 199.8 (d, J=3.8 Hz), 160.7 (d, J=251.9 Hz), 158.5, 133.8 (d, J=8.8 Hz), 132.3, 130.9 (d, J=2.8 Hz), 129.1, 126.0 (d, J=12.8 Hz), 124.2 (d, J=3.9 Hz), 116.4 (d, J=23.7 Hz), 114.0, 55.0, 50.9 (d, J=5.9 Hz), 18.8; $^{19}$F NMR (282 MHz, CDCl$_3$) 6-100.1; IR (neat) v (cm$^{-1}$) 3069, 3034, 2974, 2933, 2871, 2836, 1682, 1609, 1582, 1513, 1480, 1451, 1422, 1373, 1324, 1303, 1274, 1254, 1211, 1179, 1153, 1105, 1034, 1005; MS (70 eV, EI) m/z (%): 259 (M$^+$+1, 0.99), 258 (M$^+$, 5.49), 135 (100); HRMS calcd for C$_{16}$H$_{15}$O$_2$F (M$^+$): 258.1056. Found: 258.1057.

Example 11

2-[3'-(N,N-dimethylamino)phenyl]-1-phenyl-1-propanone

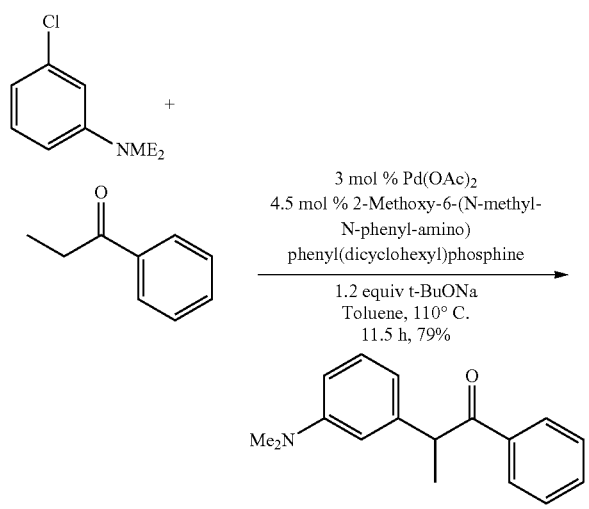

This reaction is carried out in the same manner as the reaction in example 3. The difference is that, the reactants are 3-chloro-N,N-dimethylaniline (155.9 mg, 1.0 mmol), propiophenone (160.9 mg, 1.2 mmol), palladium acetate (6.7 mg, 0.030 mmol), 2-Methoxy-6-(N-methyl-N-phenyl-amino)phenyl(dicyclohexyl)phosphine (18.4 mg, 0.045 mmol), t-BuONa (116.1 mg, 1.2 mmol) in 3 mL dry toluene at 110° C. for 11.5 h. 2-[3'-(N, N-dimethylamino)phenyl]-1-phenyl-1-propanone (200.7 mg) was obtained with a yield of 79% as liquid. $^1$H NMR (300 MHz, CDCl$_3$) δ 8.03-7.97 (m, 2H, ArH), 7.52-7.44 (m, 1H, ArH), 7.43-7.35 (m, 2H, ArH), 7.20-7.11 (m, 1H, ArH), 6.65-6.55 (m, 3H, ArH), 4.19 (s, 2H, CH$_2$), 2.87 (s, 6H, 2×CH$_3$); $^{13}$C NMR (75 MHz, CDCl$_3$) δ 197.7, 150.6, 136.4, 135.1, 132.8, 129.1, 128.5, 128.4, 117.4, 113.1, 110.9, 45.9, 40.3; IR (neat) v (cm$^{-1}$) 3056, 2891, 2804, 1679, 1601, 1579, 1501, 1447, 1354, 1330, 1276, 1205, 1180, 1155, 1062; MS (70 eV, EI) m/z (%): 240 (M$^+$+1, 10.27), 239 (M$^+$, 54.99), 105 (100); HRMS calcd for C$_{16}$H$_{17}$NO (M$^+$): 239.1310. Found: 239.1309.

Example 12

2-(4'-Fluorophenyl)-1-(4'-methoxyphenyl)-1-propanone

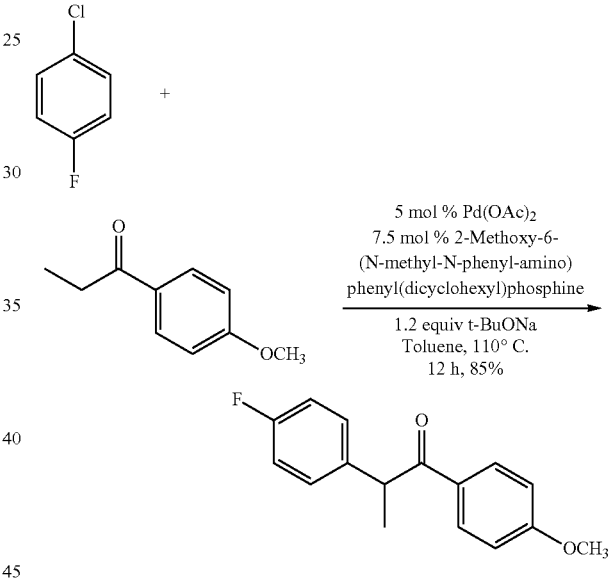

This reaction is carried out in the same manner as the reaction in example 3. The difference is that, the reactants are 4-fluorophenyl chloride (130.2 mg, 1.0 mmol), 1-(4-methoxyphenyl)-1-propanone (198.4 mg, 1.2 mmol), palladium acetate (11.1 mg, 0.050 mmol), 2-Methoxy-6-(N-methyl-N-phenyl-amino)phenyldicyclohexyl)phosphine (30.8 mg, 0.075 mmol), t-BuONa (115.0 mg, 1.2 mmol) in 3 mL dry toluene at 110° C. for 12 h. 2-(4'-Fluorophenyl)-1-(4'-methoxyphenyl)-1-propanone (252.8 mg, containing 19% of 1-(4-methoxyphenyl)-1-propanone as determined by $^1$H NMR analysis) was obtained with a yield of 85% as solid. m.p.: 83.3-84.0° C. (n-hexane/ethyl acetate); $^1$H NMR (300 MHz, CDCl$_3$) δ 7.98-7.89 (m, 2H, ArH), 7.29-7.20 (m, 2H, ArH), 7.00-6.81 (m, 4H, ArH), 4.64 (q, J=6.9 Hz, 1H, CH), 3.76 (s, 3H, OCH$_3$), 1.49 (d, J=6.9 Hz, 3H, CH$_3$); $^{13}$C NMR (75 MHz, CDCl$_3$) δ 198.5, 163.1, 159.9, 137.4 (d, J=2.9 Hz), 130.8, 129.0 (d, J=8.6 Hz), 128.9, 115.5 (d, J=21.0 Hz), 113.5, 55.2, 46.3, 19.4; $^{19}$F NMR (282 MHz, CDCl$_3$) δ −115.9; IR (KBr) v (cm$^{-1}$) 3072, 2975, 2934, 2840, 1674, 1600, 1574, 1510, 1456, 1419, 1373, 1338, 1311, 1258, 1225, 1171, 1114, 1030;

MS (70 eV, EI) m/z (%): 258 (M+, 0.32), 135 (100); Anal. Calcd. for $C_{16}H_{15}FO_2$: C, 74.40; H, 5.85. Found: C, 74.23; H, 5.82.

Example 13

2-(4'-Methoxyphenyl)-1-phenyl-1-ethanone

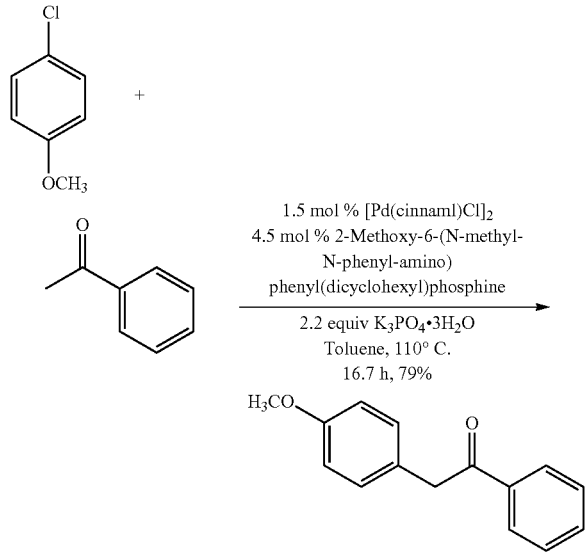

This reaction is carried out in the same manner as the reaction in example 3. The difference is that, the reactants are p-methoxyphenyl chloride (142.2 mg, 1.0 mmol), acetophenone (302.1 mg, 2.5 mmol), palladium cinnamyl chloride (7.8 mg, 0.015 mmol), 2-Methoxy-6-(N-methyl-N-phenyl-amino)phenyldicyclohexyl)phosphine (18.4 mg, 0.045 mmol), $K_3PO_4 \cdot 3H_2O$ (664.0 mg, 2.5 mmol) in 3 mL dry toluene at 110° C. for 16.7 h. 2-(4'-Methoxyphenyl)-1-phenyl-1-ethanone (177.3 mg) was obtained with a yield of 79% as solid. m.p.: 94.1-94.4° C. (n-hexane); $^1$H NMR (300 MHz, CDCl$_3$) δ 8.07-8.00 (m, 2H, ArH), 7.60-7.51 (m, 1H, ArH), 7.51-7.42 (m, 2H, ArH), 7.25-7.17 (m, 2H, ArH), 6.92-6.86 (m, 2H, ArH), 4.24 (s, 2H, CH$_2$), 3.78 (s, 3H, OCH$_3$); $^{13}$C NMR (75 MHz, CDCl$_3$) δ 197.8, 158.3, 136.4, 132.9, 130.3, 128.45, 128.41, 126.3, 113.9, 55.0, 44.4; IR (KBr) v (cm$^{-1}$) 3056, 2998, 2954, 2934, 2905, 2835, 1691, 1612, 1596, 1579, 1514, 1463, 1447, 1411, 1335, 1301, 1245, 1218, 1204, 1178, 1107, 1035; MS (70 eV, EI) m/z (%): 227 (M$^+$+1, 3.58), 226 (M$^+$, 21.25), 121 (100).

Example 14

2-(4'-Methylphenyl)-1-phenyl-1-ethanone

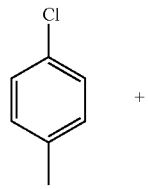

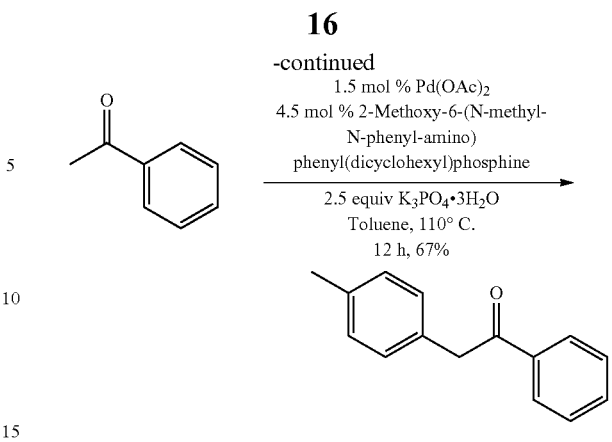

This reaction is carried out in the same manner as the reaction in example 3. The difference is that, the reactants are p-methylphenyl chloride (125.6 mg, 1.0 mmol), acetophenone (300.1 mg, 2.5 mmol), palladium cinnamyl chloride (7.8 mg, 0.015 mmol), 2-Methoxy-6-(N-methyl-N-phenyl-amino)phenyldicyclohexyl)phosphine (18.3 mg, 0.045 mmol), $K_3PO_4 \cdot 3H_2O$ (665.8 mg, 2.5 mmol) in 3 mL dry toluene at 110° C. for 12 h. 2-(4'-Methylphenyl)-1-phenyl-1-ethanone (140.5 mg) was obtained with a yield of 67% as solid. m.p.: 95.8-96.1° C. (n-hexane); $^1$H NMR (300 MHz, CDCl$_3$) δ 8.07-8.00 (m, 2H, ArH), 7.62-7.53 (m, 1H, ArH), 7.52-7.43 (m, 2H, ArH), 7.22-7.13 (m, 4H, ArH), 4.27 (s, 2H, CH$_2$), 2.35 (s, 3H, CH$_3$); $^{13}$C NMR (75 MHz, CDCl$_3$) δ 197.7, 136.5, 136.3, 133.0, 131.3, 129.3, 129.2, 128.5, 45.0, 21.0; IR (KBr) v (cm$^{-1}$) 3051, 3024, 2896, 1686, 1592, 1578, 1515, 1448, 1406, 1335, 1221, 1209, 1197, 1181; MS (70 eV, EI) m/z (%): 211 (M$^+$+1, 0.65), 210 (M$^+$, 3.47), 105 (100).

Example 15

2-(3'-Methoxyphenyl)-1-phenyl-1-ethanone

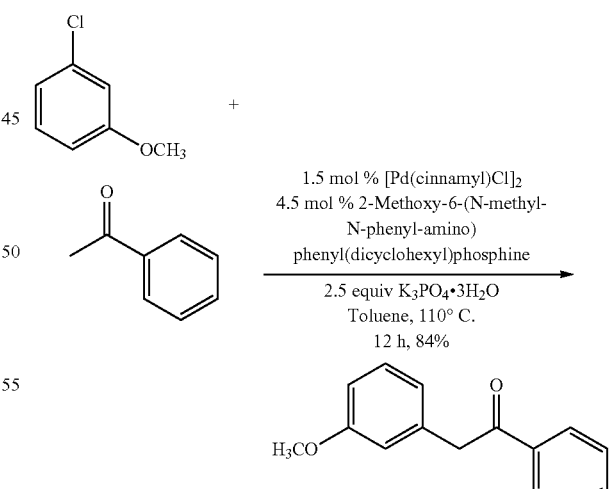

This reaction is carried out in the same manner as the reaction in example 3. The difference is that, the reactants are m-methoxyphenyl chloride (142.7 mg, 1.0 mmol), acetophenone (299.9 mg, 2.5 mmol), palladium cinnamyl chloride (7.8 mg, 0.015 mmol), 2-Methoxy-6-(N-methyl-N-phenyl-amino)phenyldicyclohexyl)phosphine (18.3 mg, 0.045 mmol), K$_3$PO$_4$3H$_2$O (663.9 mg, 2.5 mmol) in 3 mL dry toluene at 110° C. for 12 h. 2-(3'-Methoxylphenyl)-1-phenyl-1-ethanone (189.0 mg) was obtained with a yield of 84% as liquids. $^1$H NMR (300 MHz, CDCl$_3$) δ 8.02-7.96 (m, 2H, ArH), 7.55-7.47 (m, 1H, ArH), 7.46-7.38 (m, 2H, ArH), 7.21 (t, J=7.8 Hz, 1H, ArH), 6.87-6.73 (m, 3H, ArH), 4.22 (s, 2H, CH$_2$), 3.73 (s, 3H, OCH$_3$); $^{13}$C NMR (75 MHz, CDCl$_3$) δ 197.3, 159.6, 136.3, 135.9, 133.0, 129.5, 128.47, 128.45, 121.6, 115.0, 112.2, 55.0, 45.4; IR (neat) v (cm$^{-1}$) 3058, 3002, 2938, 2835, 1682, 1597, 1490, 1448, 1317, 1263, 1211, 1153, 1050, 1020, 1001; MS (70 eV, EI) m/z (%): 227 (M$^+$+1, 2.28), 226 (M$^+$, 12.78), 105 (100).

Example 16

2-(3'-Methoxyphenyl)-1-(2'-naphthyl)-1-ethanone

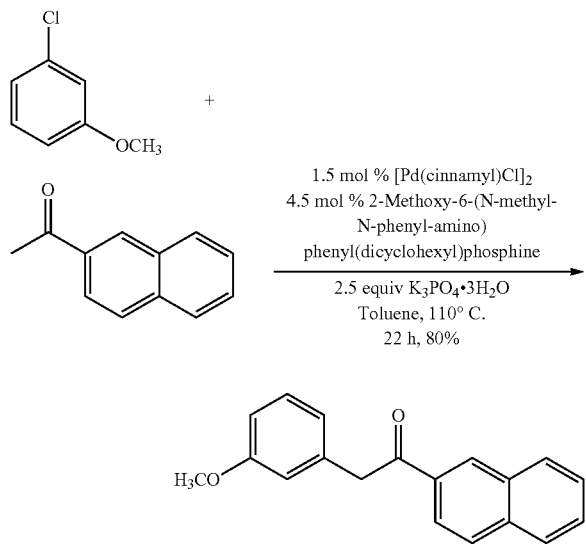

This reaction is carried out in the same manner as the reaction in example 3. The difference is that, the reactants are m-methoxyphenyl chloride (143.3 mg, 1.0 mmol), 1-(2-naphthyl)ethanone (426.3 mg, 2.5 mmol), palladium cinnamyl chloride (7.9 mg, 0.015 mmol), 2-Methoxy-6-(N-methyl-N-phenyl-amino)phenyldicyclohexyl)phosphine (18.5 mg, 0.045 mmol), K$_3$PO$_4$:3H$_2$O (665.3 mg, 2.5 mmol) in 3 mL dry toluene at 110° C. for 22 h. 2-(3'-Methoxyphenyl)-1-(2'-naphthyl)-1-ethanone (222.0 mg) was obtained with a yield of 80% as solid. m.p.: 67.3-68.4° C. (n-Hexane/Ethyl acetate); $^1$H NMR (300 MHz, CDCl$_3$) δ 8.49 (s, 1H, ArH), 8.05-7.99 (m, 1H, ArH), 7.92-7.86 (m, 1H, ArH), 7.85-7.77 (m, 2H, ArH), 7.59-7.45 (m, 2H, ArH), 7.21 (t, J=7.8 Hz, 1H, ArH), 6.91-6.82 (m, 2H, ArH), 6.80-6.73 (m, 1H, ArH), 4.32 (s, 2H, CH$_2$), 3.72 (s, 3H, OCH$_3$); $^{13}$C NMR (75 MHz, CDCl$_3$) δ 197.3, 159.6, 136.0, 135.4, 133.7, 132.3, 130.3, 129.5, 129.4, 128.4, 128.3, 127.6, 126.6, 124.1, 121.7, 115.0, 112.2, 55.0, 45.4; IR (KBr) v (cm$^{-1}$) 3056, 2937, 2835, 1677, 1625, 1597, 1584, 1561, 1490, 1467, 1437, 1383, 1352, 1265, 1152, 1123, 1048; MS (70 eV, EI) m/z (%): 277 (M$^+$+1, 2.13), 276 (M$^+$, 9.94), 155 (100); Anal. Calcd. for C$_{19}$H$_{16}$O$_2$: C, 82.58; H, 5.84. Found: C, 82.65; H, 5.81.

Example 17

2-(4'-Methoxyphenyl)-1-(1'-naphthyl)-1-ethanone

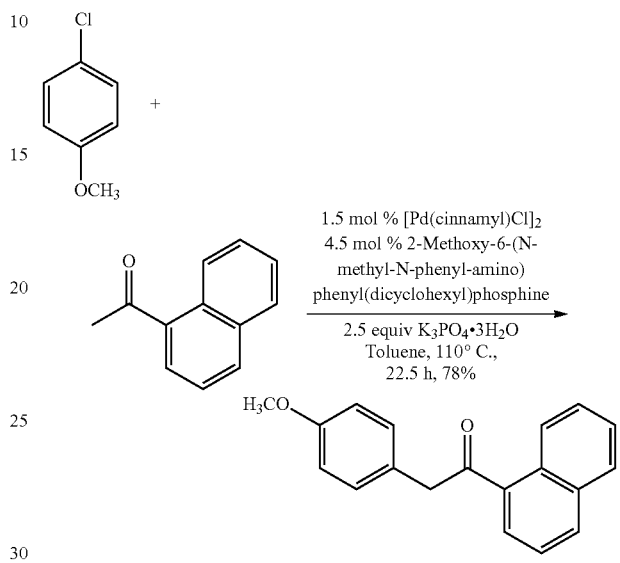

This reaction is carried out in the same manner as the reaction in example 3. The difference is that, the reactants are p-methoxyphenyl chloride (142.8 mg, 1.0 mmol), 1-(1-naphthyl)ethanone (424.4 mg, 2.5 mmol), palladium cinnamyl chloride (7.4 mg, 0.015 mmol), 2-Methoxy-6-(N-methyl-N-phenyl-amino)phenyldicyclohexyl)phosphine (18.3 mg, 0.045 mmol), K$_3$PO$_4$3H$_2$O (665.2 mg, 2.5 mmol) in 3 mL dry toluene at 110° C. for 22.5 h. 2-(4'-Methoxyphenyl)-1-(1'-naphthyl)-1-ethanone (215.1 mg) was obtained with a yield of 78% as solid. m.p.: 74.7-75.4° C. (n-Hexane/Ethyl acetate); $^1$H NMR (300 MHz, CDCl$_3$) δ 8.56 (d, J=8.4 Hz, 1H, ArH), 7.91-7.84 (m, 2H, ArH), 7.82-7.75 (m, 1H, ArH), 7.53-7.36 (m, 3H, ArH), 7.20-7.12 (m, 2H, ArH), 6.86-6.77 (m, 2H, ArH), 4.23 (s, 2H, CH$_2$), 3.67 (s, 3H, OCH$_3$); $^{13}$C NMR (75 MHz, CDCl$_3$) δ 201.7, 158.3, 135.3, 133.7, 132.5, 130.4, 130.2, 128.2, 127.74, 127.68, 126.31, 126.26, 125.6, 124.1, 113.9, 55.0, 47.8; IR (KBr) v (cm$^{-1}$) 3053, 3033, 3002, 2953, 2938, 2909, 2833, 1685, 1611, 1512, 1467, 1311, 1302, 1243, 1214, 1182, 1169, 1104, 1088, 1034; MS (70 eV, EI) m/z (%): 277 (M$^+$+1, 1.24), 276 (M$^+$, 6.24), 155 (100).

Example 18

2-(4'-Methoxyphenyl)-1-(m-tolyl)-1-ethanone

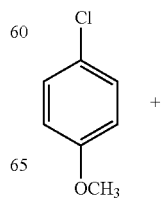

-continued

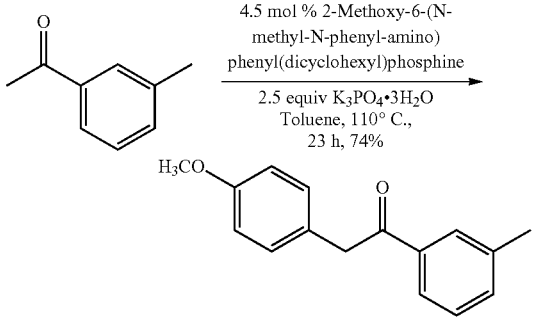

This reaction is carried out in the same manner as the reaction in example 3. The difference is that, the reactants are p-methoxyphenyl chloride (141.7 mg, 1.0 mmol), 1-(m-tolyl)ethanone (336.2 mg, 2.5 mmol), palladium cinnamyl chloride (7.8 mg, 0.015 mmol), 2-Methoxy-6-(N-methyl-N-phenyl-amino)phenyldicyclohexyl)phosphine (18.4 mg, 0.045 mmol), $K_3PO_4 \cdot 3H_2O$ (664.9 mg, 2.5 mmol) in 3 mL dry toluene at 110° C. for 23 h. 2-(4'-Methoxyphenyl)-1-(m-tolyl)-1-ethanone (176.4 mg) was obtained with a yield of 74% as solid. m.p.: 56.7-57.8° C. (n-hexane); $^1$H NMR (300 MHz, CDCl$_3$) δ 7.82-7.75 (m, 2H, ArH), 7.36-7.27 (m, 2H, ArH), 7.20-7.10 (m, 2H, ArH), 6.88-6.79 (m, 2H, ArH), 4.18 (s, 2H, CH$_2$), 3.73 (s, 3H, OCH$_3$), 2.37 (s, 3H, ArCH$_3$); $^{13}$C NMR (75 MHz, CDCl$_3$) δ 198.0, 158.3, 138.2, 136.4, 133.7, 130.3, 128.9, 128.3, 126.4, 125.7, 113.9, 55.0, 44.4, 21.2; IR (KBr) v (cm$^{-1}$) 3034, 2999, 2933, 2835, 1694, 1682, 1614, 1585, 1515, 1463, 1301, 1282, 1246, 1178, 1156, 1107, 1035, 1000; MS (70 eV, EI) m/z (%): 241 (M$^+$+1, 1.89), 240 (M$^+$, 10.02), 119 (100); Anal. Calcd. for C$_{16}$H$_{16}$O$_2$: C, 79.97; H, 6.71. Found: C, 79.71; H, 6.69.

Example 19

1-(4'-Fluorophenyl)-2-(3'-methoxyphenyl)-1-ethanone

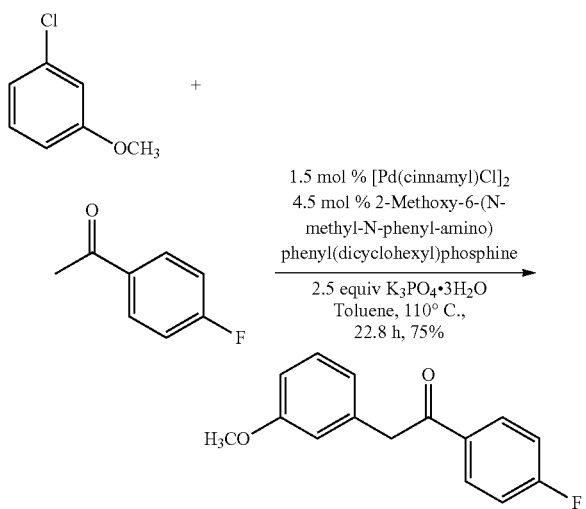

This reaction is carried out in the same manner as the reaction in example 3. The difference is that, the reactants are m-methoxyphenyl chloride (143.7 mg, 1.0 mmol), 1-(4'-fluorophenyl)ethanone (347.2 mg, 2.5 mmol), palladium cinnamyl chloride (7.8 mg, 0.015 mmol), 2-Methoxy-6-(N-methyl-N-phenyl-amino)phenyldicyclohexyl)phosphine (18.4 mg, 0.045 mmol), $K_3PO_4 \cdot 3H_2O$ (664.2 mg, 2.5 mmol) in 3 mL dry toluene at 110° C. for 22.8 h. 1-(4'-Fluorophenyl)-2-(3'-methoxyphenyl)-1-ethanone (185.5 mg) was obtained with a yield of 75% as liquid. $^1$H NMR (300 MHz, CDCl$_3$) δ 8.05-7.98 (m, 2H, ArH), 7.27-7.18 (m, 1H, ArH), 7.12-7.04 (m, 2H, ArH), 6.86-6.75 (m, 3H, ArH), 4.20 (s, 2H, CH$_2$), 3.75 (s, 3H, OCH$_3$); $^{13}$C NMR (75 MHz, CDCl$_3$) δ 195.8, 167.2, 163.9, 159.7, 135.7, 132.8, 132.7, 131.2, 131.1, 129.6, 121.6, 115.7, 115.4, 115.0, 112.2, 55.0, 45.4; $^{19}$F NMR (282 MHz, CDCl$_3$) 6-104.9; IR (neat) v (cm$^{-1}$) 3072, 3002, 2940, 2836, 1682, 1597, 1506, 1491, 1455, 1437, 1331, 1264, 1232, 1157, 1099, 1050, 1002; MS (70 eV, EI) m/z (%): 245 (M$^+$+1, 3.27), 244 (M$^+$, 17.36), 123 (100).

Example 20

2-[3'-(N,N-dimethylamino)phenyl]-1-phenyl-1-propanone

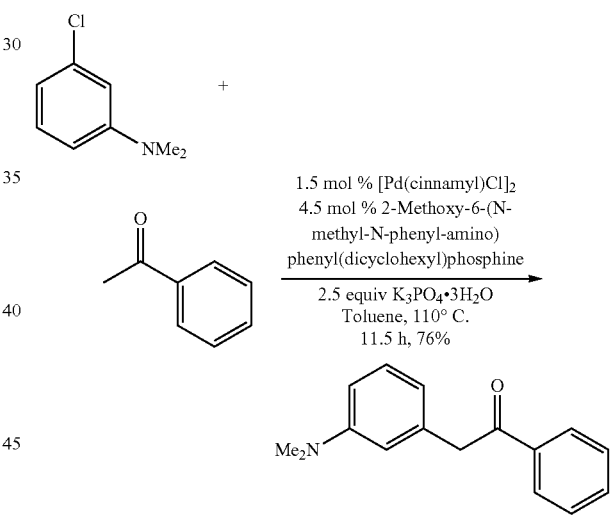

This reaction is carried out in the same manner as the reaction in example 3. The difference is that, the reactants are 3'-(N,N-dimethylamino)phenyl chloride (156.6 mg, 1.0 mmol), acetophenone (299.6 mg, 2.5 mmol), palladium cinnamyl chloride (7.8 mg, 0.015 mmol), 2-Methoxy-6-(N-methyl-N-phenyl-amino)phenyldicyclohexyl)phosphine (18.5 mg, 0.045 mmol), $K_3PO_4 \cdot 3H_2O$ (666.4 mg, 2.5 mmol) in 3 mL dry toluene at 110° C. for 11.5 h. 2-[3'-(N,N-dimethylamino)phenyl]-1-phenyl-1-propanone (183.9 mg) was obtained with a yield of 76% as liquid. $^1$H NMR (300 MHz, CDCl$_3$) δ 8.03-7.97 (m, 2H, ArH), 7.52-7.44 (m, 1H, ArH), 7.43-7.35 (m, 2H, ArH), 7.20-7.11 (m, 1H, ArH), 6.65-6.55 (m, 3H, ArH), 4.19 (s, 2H, CH$_2$), 2.87 (s, 6H, 2×CH$_3$); $^{13}$C NMR (75 MHz, CDCl$_3$) δ 197.7, 150.6, 136.4, 135.1, 132.8, 129.1, 128.5, 128.4, 117.4, 113.1, 110.9, 45.9, 40.3; IR (neat) v (cm$^{-1}$) 3056, 2891, 2804, 1679, 1601, 1579, 1501, 1447, 1354, 1330, 1276, 1205, 1180, 1155, 1062; MS (70 eV, EI)

m/z (%): 240 (M++1, 10.27), 239 (M+, 54.99), 105 (100); HRMS calcd for $C_{16}H_{17}NO$ (M+): 239.1310. Found: 239.1309.

Example 21

1-Phenyl-2-(2'-methyl-7'-quinolyl)-1-ethanone

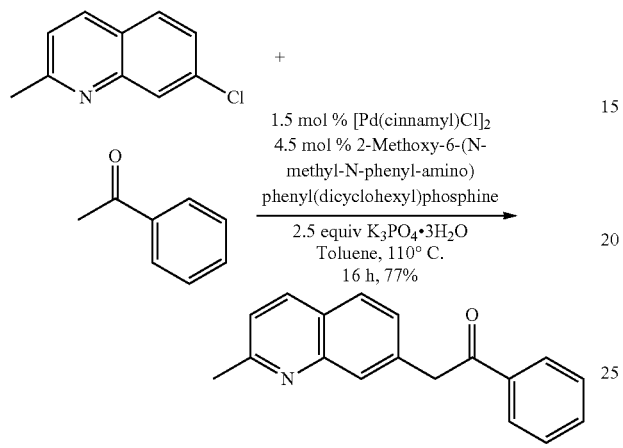

This reaction is carried out in the same manner as the reaction in example 3. The difference is that, the reactants are 2-methyl-7-quinolyl chloride (177.3 mg, 1.0 mmol), acetophenone (301.1 mg, 2.5 mmol), palladium cinnamyl chloride (7.8 mg, 0.015 mmol), 2-Methoxy-6-(N-methyl-N-phenyl-amino)phenyldicyclohexyl)phosphine (18.5 mg, 0.045 mmol), $K_3PO_4·3H_2O$ (664.4 mg, 2.5 mmol) in 3 mL dry toluene at 110° C. for 16 h. 1-Phenyl-2-(2'-methyl-7'-quinolyl)-1-ethanone (200.4 mg) was obtained with a yield of 77% as solid. m.p.: 70.4-71.6° C. (n-Hexane/Ethyl acetate); $^1H$ NMR (300 MHz, $CDCl_3$) δ 8.06-8.00 (m, 2H, ArH), 7.99-7.88 (m, 2H, ArH), 7.72-7.65 (m, 1H, ArH), 7.55-7.47 (m, 1H, ArH), 7.46-7.35 (m, 3H, ArH), 7.22-7.15 (m, 1H, ArH), 4.45 (s, 2H, $CH_2$), 2.70 (s, 3H, $CH_3$); $^{13}C$ NMR (75 MHz, $CDCl_3$) δ 197.0, 159.0, 147.7, 136.1, 136.0, 135.7, 133.1, 128.8, 128.5, 127.6, 127.1, 125.1, 121.7, 45.6, 25.2; IR (KBr) v (cm$^{-1}$) 3055, 2920, 2849, 1687, 1625, 1599, 1509, 1448, 1417, 1328, 1306, 1281, 1209, 1182, 1123; MS (70 eV, EI) m/z (%): 262 (M++1, 3.65), 261 (M+, 16.62), 105 (100); Anal. Calcd. for $C_{18}H_{15}NO$: C, 82.73; H, 5.79; N, 5.36. Found: C, 82.34; H, 5.91; N, 5.27.

Example 22

1-(4'-Methoxyphenyl)-2-propanone

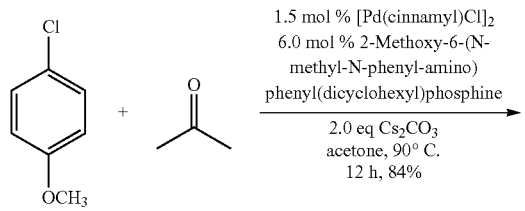

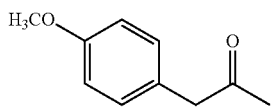

This reaction is carried out in the same manner as the reaction in example 3. The difference is that, the reactants are p-methoxyphenyl chloride (143.2 mg, 1.0 mmol), palladium cinnamyl chloride (7.9 mg, 0.015 mmol), 2-Methoxy-6-(N-methyl-N-phenyl-amino)phenyldicyclohexyl)phosphine (24.5 mg, 0.060 mmol), $Cs_2CO_3$ (651.0 mg, 2.0 mmol) in 4.0 mL acetone at 90° C. for 12 h. 1-(4'-Methoxyphenyl)-2-propanone (137.9 mg) was obtained with a yield of 84% as liquid. $^1H$ NMR (300 MHz, $CDCl_3$) δ 7.15-7.07 (m, 2H, ArH), 6.92-6.82 (m, 2H, ArH), 3.79 (s, 3H, $OCH_3$), 3.63 (s, 2H, $CH_2$), 2.13 (s, 3H, $COCH_3$); $^{13}C$ NMR (75 MHz, $CDCl_3$) δ 206.8, 158.5, 130.3, 126.1, 114.0, 55.1, 50.0, 29.0; IR (neat) v (cm$^{-1}$) 3002, 2957, 2935, 2911, 2837, 1713, 1612, 1584, 1514, 1464, 1442, 1423, 1356, 1301, 1249, 1179, 1158, 1109, 1034; MS (70 eV, EI) m/z (%): 165 (M++1, 2.58), 164 (M+, 23.60), 121 (100).

Example 23

1-(2',6'-Dimethylphenyl)-2-propanone

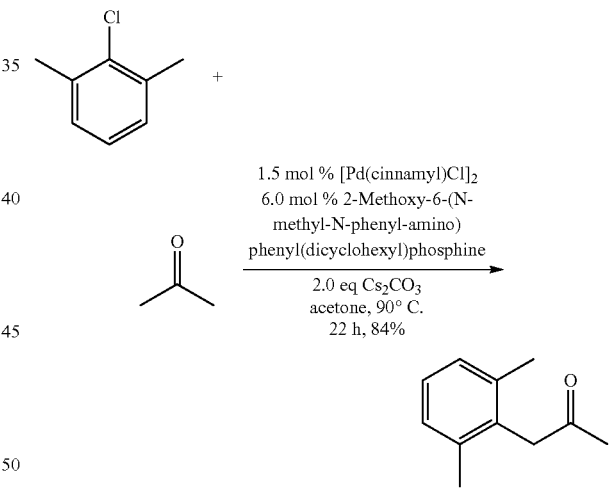

This reaction is carried out in the same manner as the reaction in example 3. The difference is that, the reactants are 2,6-dimethylphenyl chloride (142.4 mg, 1.0 mmol), palladium cinnamyl chloride (7.8 mg, 0.015 mmol), 2-Methoxy-6-(N-methyl-N-phenyl-amino)phenyldicyclohexyl)phosphine (24.4 mg, 0.060 mmol), $Cs_2CO_3$ (651.9 mg, 2.0 mmol) in 4.0 mL acetone at 90° C. for 22 h. 1-(2',6'-Dimethylphenyl)-2-propanone (138.4 mg) was obtained with a yield of 84% as liquid. $^1H$ NMR (300 MHz, $CDCl_3$) δ 7.15-7.03 (m, 3H, ArH), 3.79 (s, 2H, $CH_2$), 2.27 (s, 6H, $2×ArCH_3$), 2.17 (s, 3H, $COCH_3$); $^{13}C$ NMR (75 MHz, $CDCl_3$) δ 206.2, 136.7, 132.1, 128.1, 126.9, 45.0, 29.2, 20.2; IR (neat) v (cm$^{-1}$) 3021, 2922, 2867, 1715, 1589, 1470, 1446, 1415, 1379, 1357, 1317, 1223, 1158, 1095, 1053, 1031; MS (70 eV, EI) m/z (%): 163

($M^++1$, 3.30), 162 ($M^+$, 27.85), 119 (100); HRMS calcd for $C_{11}H_{14}O$ ($M^+$): 162.1045. Found: 162.1046.

Example 24

1-(p-Tolyl)-2-propanone

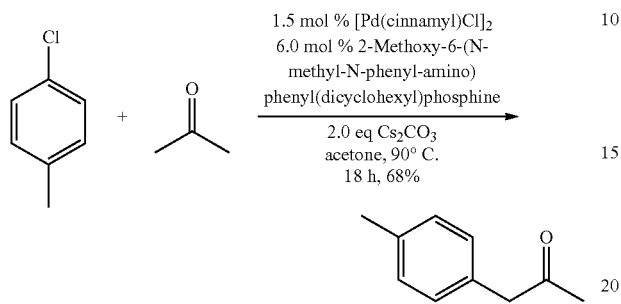

This reaction is carried out in the same manner as the reaction in example 3. The difference is that, the reactants are p-methylphenyl chloride (127.0 mg, 1.0 mmol), palladium cinnamyl chloride (7.9 mg, 0.015 mmol), 2-Methoxy-6-(N-methyl-N-phenyl-amino) henyldicyclohexyl)phosphine (24.3 mg, 0.060 mmol), $Cs_2CO_3$ (652.2 mg, 2.0 mmol) in 4.0 mL acetone at 90° C. for 18 h. 1-(p-tolyl)-2-propanone (100.5 mg) was obtained with a yield of 68% as liquid. $^1H$ NMR (300 MHz, $CDCl_3$) δ 7.19-7.05 (m, 4H, ArH), 3.66 (s, 2H, $CH_2$), 2.34 (s, 3H, $ArCH_3$), 2.15 (s, 3H, $COCH_3$); $^{13}C$ NMR (75 MHz, $CDCl_3$) δ 206.7, 136.6, 131.1, 129.4, 129.2, 50.6, 29.1, 21.0; IR (neat) v ($cm^{-1}$) 3023, 3004, 2922, 2857, 1714, 1615, 1514, 1417, 1356, 1229, 1158, 1040, 1023; MS (70 eV, EI) m/z (%): 149 ($M^++1$, 3.90), 148 ($M^+$, 31.26), 105 (100).

Example 25

1-(2'-Methoxyphenyl)-2-propanone

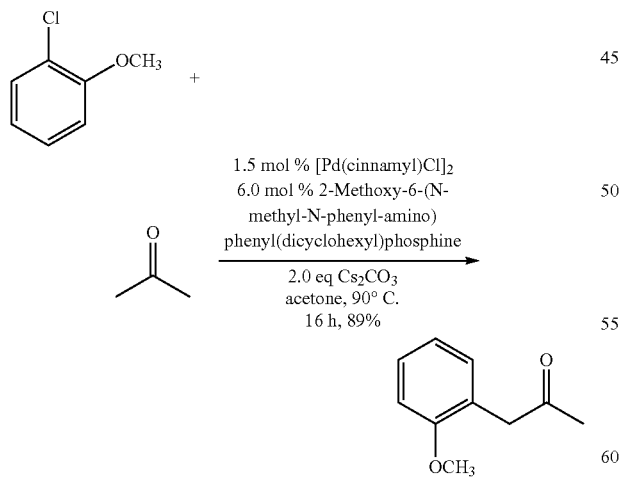

This reaction is carried out in the same manner as the reaction in example 3. The difference is that, the reactants are o-methoxyphenyl chloride (142.3 mg, 1.0 mmol), palladium cinnamyl chloride (7.9 mg, 0.015 mmol), 2-Methoxy-6-(N-methyl-N-phenyl-amino) henyldicyclohexyl)phosphine (24.5 mg, 0.060 mmol), $Cs_2CO_3$ (653.0 mg, 2.0 mmol) in 4.0 mL acetone at 90° C. for 16 h. 1-(2'-Methoxyphenyl)-2-propanone (147.7 mg) was obtained with a yield of 89% as liquid. $^1H$ NMR (300 MHz, $CDCl_3$) δ 7.29-7.22 (m, 1H, ArH), 7.14-7.09 (m, 1H, ArH), 6.94-6.84 (m, 2H, ArH), 3.79 (s, 3H, $OCH_3$), 3.66 (s, 2H, $CH_2$), 2.12 (s, 3H, $COCH_3$); $^{13}C$ NMR (75 MHz, $CDCl_3$) δ 206.9, 157.2, 131.0, 128.4, 123.5, 120.5, 110.3, 55.2, 45.4, 29.1; IR (neat) v ($cm^{-1}$) 3003, 2941, 2905, 2837, 1713, 1602, 1589, 1496, 1464, 1439, 1356, 1322, 1290, 1247, 1176, 1160, 1115, 1050, 1030; MS (70 eV, EI) m/z (%): 165 ($M^++1$, 6.45), 164 ($M^+$, 50.19), 91 (100).

Example 26

1-(4'-tert-Butylphenyl)-2-propanone

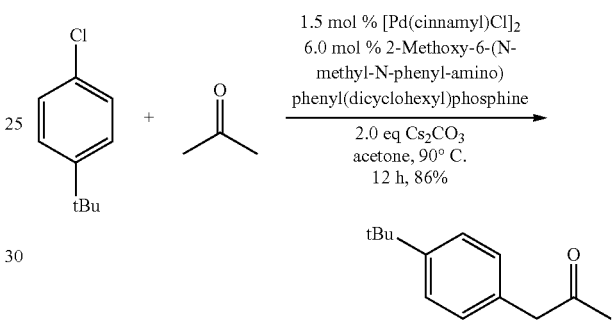

This reaction is carried out in the same manner as the reaction in example 3. The difference is that, the reactants are 4'-tert-Butylphenyl I chloride (167.4 mg, 1.0 mmol), palladium cinnamyl chloride (7.9 mg, 0.015 mmol), 2-Methoxy-6-(N-methyl-N-phenyl-amino) henyldicyclohexyl)phosphine (24.4 mg, 0.060 mmol), $Cs_2CO_3$ (653.4 mg, 2.0 mmol) in 4.0 mL acetone at 90° C. for 12 h. 1-(4'-tert-Butylphenyl)-2-propanone (163.6 mg) was obtained with a yield of 86% as liquid. $^1H$ NMR (300 MHz, $CDCl_3$) δ 7.40-7.35 (m, 2H, ArH), 7.18-7.12 (m, 2H, ArH), 3.68 (s, 2H, $CH_2$), 2.17 (s, 3H, $COCH_3$), 1.33 (s, 9H, $3 \times CH_3$); $^{13}C$ NMR (75 MHz, $CDCl_3$) δ 206.9, 149.8, 131.0, 128.9, 125.6, 50.4, 34.4, 31.2, 29.2; IR (neat) v ($cm^{-1}$) 3027, 2962, 2905, 2869, 1713, 1514, 1463, 1416, 1394, 1357, 1326, 1269, 1229, 1203, 1158, 1110, 1020; MS (70 eV, EI) m/z (%): 191 ($M^++1$, 4.99), 190 ($M^+$, 30.84), 147 (100).

Example 27

1-[3'-(N,N-Dimethylamino)phenyl]-2-propanone

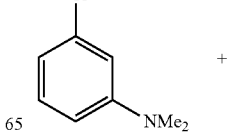

1.5 mol % [Pd(cinnamyl)Cl]₂
6.0 mol % 2-Methoxy-6-(N-methyl-N-phenyl-amino)phenyl(dicyclohexyl)phosphine
———————————————→
2.0 eq Cs₂CO₃
acetone, 90° C.
11.5 h, 69%

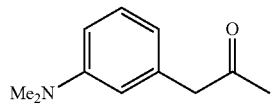

This reaction is carried out in the same manner as the reaction in example 3. The difference is that, the reactants are 3-(N,N-Dimethylamino)phenyl chloride (156.0 mg, 0.99 mmol), palladium cinnamyl chloride (7.8 mg, 0.015 mmol), 2-Methoxy-6-(N-methyl-N-phenyl-amino)henyldicyclohexyl)phosphine (24.6 mg, 0.060 mmol), Cs₂CO₃ (653.2 mg, 2.0 mmol) in 4.0 mL acetone at 90° C. for 12 h. 1-[3'-(N,N-Dimethylamino)phenyl]-2-propanone (122.2 mg) was obtained with a yield of 69% as liquid. $^1$H NMR (300 MHz, CDCl₃) δ 7.21 (t, J=7.8 Hz, 1H, ArH), 6.69-6.62 (m, 1H, ArH), 6.61-6.53 (m, 2H, ArH), 3.64 (s, 2H, CH₂), 2.95 (s, 6H, N(CH₃)₂), 2.15 (s, 3H, COCH₃); $^{13}$C NMR (75 MHz, CDCl₃) δ 207.0, 150.7, 135.0, 129.3, 117.4, 113.1, 111.1, 51.6, 40.4, 28.9; IR (neat) v (cm⁻¹) 3033, 2916, 2805, 1712, 1603, 1580, 1504, 1440, 1354, 1271, 1229, 1178, 1156, 1062; MS (70 eV, EI) m/z (%): 178 (M⁺+1, 9.69), 177 (M⁺, 73.88), 134 (100).

Example 28

1-(2'-Methyl-7'-quinolyl)-2-propanone

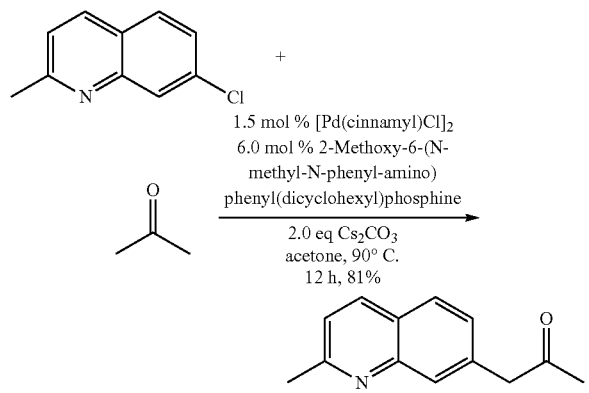

This reaction is carried out in the same manner as the reaction in example 3. The difference is that, the reactants are 2-Methyl-7-quinolyl chloride (177.7 mg, 1.0 mmol), palladium cinnamyl chloride (7.9 mg, 0.015 mmol), 2-Methoxy-6-(N-methyl-N-phenyl-amino) henyldicyclohexyl)phosphine (24.5 mg, 0.060 mmol), CS₂CO₃ (652.2 mg, 2.0 mmol) in 4.0 mL acetone at 90° C. for 12 h. 1-(2'-Methyl-7'-quinolyl)-2-propanone (162.0 mg) was obtained with a yield of 81% as solid. m.p.: 68.7-69.6° C. (n-Hexane:Ethyl acetate); $^1$H NMR (300 MHz, CDCl₃) δ 8.06-7.99 (m, 1H, ArH), 7.86 (s, 1H, ArH), 7.77-7.71 (m, 1H, ArH), 7.38-7.24 (m, 2H, ArH), 3.89 (s, 2H, CH₂), 2.74 (s, 3H, ArCH₃), 2.20 (s, 3H, COCH₃); $^{13}$C NMR (75 MHz, CDCl₃) δ 205.8, 159.3, 147.8, 135.8, 135.7, 128.9, 127.8, 127.1, 125.3, 121.9, 51.1, 29.3, 25.3; IR (KBr) v (cm⁻¹) 3050, 3001, 2921, 2853, 1713, 1626, 1606, 1545, 1510, 1420, 1357, 1304, 1222, 1159; MS (70 eV, EI) m/z (%): 200 (M⁺+1, 2.64), 199 (M⁺, 17.92), 157 (100); Anal. Calcd. for C₁₃H₁₃NO: C, 78.36; H, 6.58; N, 7.03. Found: C, 78.42; H, 6.61; N, 6.95.

Example 29

1-(1-Naphthyl)-2-propanone

This reaction is carried out in the same manner as the reaction in example 3. The difference is that, the reactants are 1-naphthyl chloride (162.1 mg, 1.0 mmol), palladium cinnamyl chloride (7.8 mg, 0.015 mmol), 2-Methoxy-6-(N-methyl-N-phenyl-amino)henyldicyclohexyl)phosphine (24.5 mg, 0.060 mmol), Cs₂CO₃ (651.9 mg, 2.0 mmol) in 4.0 mL acetone at 90° C. for 12 h. 1-(1'-naphthyl)-2-propanone (178.2 mg) was obtained with a yield of 97% as liquid. $^1$H NMR (300 MHz, CDCl₃) δ 7.96-7.87 (m, 2H, ArH), 7.87-7.80 (m, 1H, ArH), 7.60-7.44 (m, 3H, ArH), 7.42-7.37 (m, 1H, ArH), 4.12 (s, 2H, CH₂), 2.13 (s, 3H, CH₃); $^{13}$C NMR (75 MHz, CDCl₃) δ 206.7, 133.7, 132.0, 130.9, 128.6, 128.0, 127.8, 126.3, 125.7, 125.4, 123.6, 48.9, 28.8; IR (neat) v (cm⁻¹) 3046, 3006, 2918, 1712, 1596, 1510, 1417, 1398, 1356, 1320, 1229, 1163, 1021; MS (70 eV, EI) m/z (%): 185 (M⁺+1, 3.44), 184 (M⁺, 23.34), 141 (100).

Example 30

1-(4'-Benzoylphenyl)-2-propanone

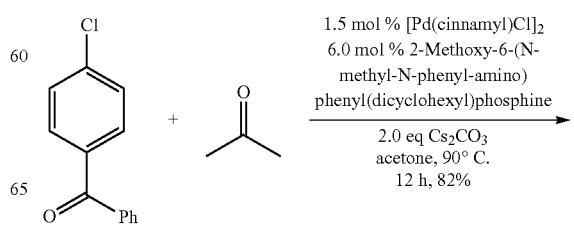

-continued

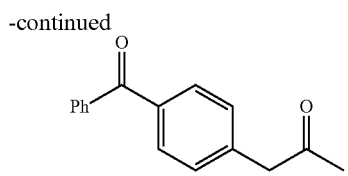

This reaction is carried out in the same manner as the reaction in example 3. The difference is that, the reactants are 4-Benzoylphenyl chloride (216.3 mg, 1.0 mmol), palladium cinnamyl chloride (7.8 mg, 0.015 mmol), 2-Methoxy-6-(N-methyl-N-phenyl-amino) henyldicyclohexyl)phosphine (24.5 mg, 0.060 mmol), $Cs_2OC_3$ (651.5 mg, 2.0 mmol) in 4.0 mL acetone at 90° C. for 12 h. 1-(4'-Benzoylphenyl)-2-propanone (195.2 mg) was obtained with a yield of 82% as liquid. $^1$H NMR (300 MHz, CDCl$_3$) δ 7.83-7.75 (m, 4H, ArH), 7.62-7.54 (m, 1H, ArH), 7.52-7.43 (m, 2H, ArH), 7.35-7.28 (m, 2H, ArH), 3.81 (s, 2H, CH$_2$), 2.22 (s, 3H, CH$_3$); $^{13}$C NMR (75 MHz, CDCl$_3$) δ 205.1, 196.1, 138.8, 137.4, 136.1, 132.3, 130.3, 129.8, 129.3, 128.1, 50.5, 29.5; IR (neat) v (cm$^{-1}$) 3059, 3003, 2917, 1715, 1660, 1651, 1606, 1579, 1447, 1416, 1358, 1317, 1278, 1227, 1178, 1159, 1113, 1075, 1020, 1001; MS (70 eV, EI) m/z (%): 239 (M$^+$+1, 0.98), 238 (M$^+$, 5.45), 196 (100).

Example 31

4-(2'-Oxopropyl)benzonitrile

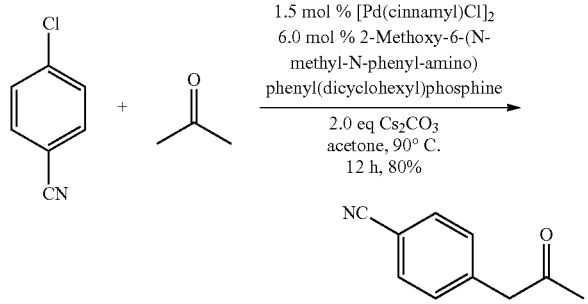

This reaction is carried out in the same manner as the reaction in example 3. The difference is that, the reactants are 4-chlorobenzonitrile (137.6 mg, 1.0 mmol), palladium cinnamyl chloride (7.9 mg, 0.015 mmol), 2-Methoxy-6-(N-methyl-N-phenyl-amino) henyldicyclohexyl)phosphine (24.5 mg, 0.060 mmol), $Cs_2CO_3$ (651.9 mg, 2.0 mmol) in 4.0 mL acetone at 90° C. for 12 h. 4-(2'-Oxopropyl)benzonitrile (127.6 mg) was obtained with a yield of 80% as solid. m.p.: 79.8-80.1° C. (n-Hexane:Ethyl acetate); $^1$H NMR (300 MHz, CDCl$_3$) δ 7.66-7.60 (m, 2H, ArH), 7.34-7.27 (m, 2H, ArH), 3.81 (s, 2H, CH$_2$), 2.23 (s, 3H, CH$_3$); $^{13}$C NMR (75 MHz, CDCl$_3$) δ 204.3, 139.3, 132.3, 130.3, 118.6, 111.0, 50.3, 29.8; IR (KBr) v (cm$^{-1}$) 3060, 3006, 2954, 2893, 2225, 1708, 1608, 1420, 1504, 1407, 1356, 1334, 1313, 1212, 1163, 1019; MS (70 eV, EI) m/z (%): 160 (M$^+$+1, 1.05), 159 (M$^+$, 9.09), 43 (100).

What is claimed:

1. A dialkyl(2-alkoxyl-6-aminophenyl)phosphine compound of the formula:

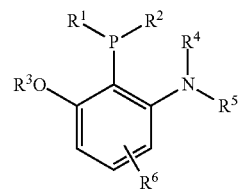

wherein
each of $R^1$ and $R^2$ is independently selected from the group consisting of isopropyl, tertbutyl, cyclopentyl, or cyclohexyl;
$R^3$ is either alkyl or aryl;
each of $R^4$ and $R^5$ is independently selected from alkyl or aryl;
$R^6$ is selected from substituted alkyl, alkoxyl, aryl, amino, thiol, carbonyl or cyano, with unfixed substituent position, the number is 0-3.

2. A preparation method for the dialkyl(2-alkoxyl-6-aminophenyl)phosphine compound of claim 1, comprising the following steps:
using n-Hexane as an organic solvent, reacting a alkoxy substituted phenyl amine with n-butyl lithium at 80° C. for 2~15 hours to produce the corresponding lithium reagent;
reacting said lithium reagent with chlorodialkyl phosphine $R^1R^2PCl$ at −78~80° C. for 2~10 hours to produce dialkyl(2-alkoxyl-6-aminophenyl)phosphine, wherein the molar ratio of said chlorodialkyl phosphine and alkoxy substituted phenyl amine lithium is 0.8~1.2:1;
wherein $R^1$, $R^2$, $R^3$, $R^4$, $R^5$ and $R^6$ are as described in claim 1.

3. The preparation method for the dialkyl(2-alkoxyl-6-aminophenyl)phosphine compound of claim 2, further comprising purifying said dialkyl(2-alkoxyl-6-aminophenyl) phosphine by re-crystallization.

* * * * *